United States Patent [19]

Ezaki et al.

[11] Patent Number: 5,520,972
[45] Date of Patent: May 28, 1996

[54] MEDICAL BAG

[75] Inventors: Tomohiko Ezaki; Yoshimasa Saito; Nobuyuki Tanaka, all of Kawasaki, Japan

[73] Assignee: Showa Denko K.K., Tokyo, Japan

[21] Appl. No.: 399,997

[22] Filed: Mar. 6, 1995

Related U.S. Application Data

[63] Continuation of Ser. No. 23,123, Feb. 26, 1993, abandoned.

[30] Foreign Application Priority Data

Apr. 22, 1992 [JP] Japan ................................. 4-103143

[51] Int. Cl.⁶ ............................ B65D 30/26; B32B 27/32; B32B 27/08
[52] U.S. Cl. .................... 428/35.2; 428/36.91; 428/213; 428/215; 428/218; 428/516; 604/403; 604/408; 383/116
[58] Field of Search ................................ 428/35.7, 36.91, 428/213, 218, 215; 383/116; 604/403, 408

[56] References Cited

U.S. PATENT DOCUMENTS

| | | | |
|---|---|---|---|
| 4,390,573 | 6/1983 | Bullard et al. | 383/116 |
| 4,481,262 | 11/1984 | Shida et al. | 428/516 |
| 4,565,720 | 1/1986 | Yaeo et al. | 428/516 |
| 4,645,482 | 2/1987 | Yoshida | 383/116 |
| 4,684,576 | 8/1987 | Tabor et al. | 428/516 |
| 4,700,838 | 10/1987 | Falciani et al. | 383/116 |
| 4,775,562 | 10/1988 | Shishido et al. | 428/35.2 |
| 4,820,557 | 4/1989 | Warren | 428/516 |
| 4,929,479 | 5/1990 | Shishido et al. | 604/408 |
| 5,000,992 | 3/1991 | Kelch | 428/516 |
| 5,026,610 | 6/1991 | Harrison | 428/516 |
| 5,128,212 | 7/1992 | Kneale et al. | 428/516 |
| 5,248,547 | 9/1993 | Wilson | 428/516 |

FOREIGN PATENT DOCUMENTS

| | | |
|---|---|---|
| 0216509 | 4/1986 | European Pat. Off. . |
| 58-165866 | 9/1983 | Japan . |
| 62-044256 | 2/1987 | Japan . |
| 62-064363 | 3/1987 | Japan . |
| 4266759 | 9/1992 | Japan . |
| 92363045 | 2/1991 | United Kingdom . |

Primary Examiner—Ellis P. Robinson
Assistant Examiner—Rena L. Dye
Attorney, Agent, or Firm—Sughrue, Mion, Zinn, Macpeak & Seas

[57] ABSTRACT

A medical bag comprised of a laminate film, sheet or tube composed of three layers or more comprising an outer layer and an inner layer, at least said inner layer of said inner and outer layers in contact with a liquid contained in the bag comprises a high-density polyethylene resin having a density of 0.945 g/cm³ or more and an Mw/Mn value of 4.0 or less or a composition comprising said high-density polyethylene resin and, added thereto, less than 60% by weight of a low-density polyethylene resin having a density of 0.930 g/cm³ or less produced by a radical polymerization; and an intermediate layer comprising a composition composed of a linear, low-density polyethylene resin having a short-chain branching and a density of 0.920 g/cm³ or less and, added thereto, less than 15% by weight of a high-density polyethylene resin having a density of 0.945 g/m³ or more and an Mw/Mn value of 4.0 or less, said inner layer, intermediate layer and outer layer being in the following relationship of a thickess ratio:

$$0.01 \leq (T_1+T_3)/(T_1+T_2+T_3) \leq 0.20$$

wherein $T_1$, $T_2$ and $T_3$ represent the thicknesses of said inner layer, intermediate layer and outer layer, respectively.

9 Claims, No Drawings

MEDICAL BAG

This is a Continuation of application Ser. No. 08/023,123, filed on Feb. 26, 1993 which is now abandoned.

BACKGROUND OF THE INVENTION

1. Field of the Invention

The present invention relates to a medical bag having excellent sanitariness, flexibility, transparency, and heat-resistance and suitable for use as a container for blood and medicinal liquids. More specifically, it relates to a medical bag composed of a sheet having a structure of three or four layers or more each comprising a polyethylene resin or the composition thereof, and is intended to provide a medical bag having excellent sanitariness, flexibility, transparency, and heat-resistance and suitable for use as a container for blood and medicinal liquids.

2. Description of the Related Art

Rigid containers made of, for example, glass, polyethylene, polypropylene or other material, and flexible bags made of poly (vinyl chloride) containing plasticizers are heretofore known as medical containers or bags. The rigid containers, however, have disadvantages in that air is introduced into the containers using a transfusion set provided with a vent needle or hole when the liquid contained therein is dropwise introduced into a human body through, for example, a vein, and therefore, the liquid contained therein might be contaminated and air can enter the vein to cause an air embolus therein. Thus, these rigid containers do not completely satisfy the requirements of sanitariness and safety. On the other hand, the flexible bags have advantages in that the introduction of air is not required and the bag itself is naturally compressed under atmospheric pressure with the dropwise introduction of the liquid contained therein, so that the safety is high and the transportation of the bag is easy. Flexible bags, however, have problems caused by, for example, plasticizers contained in polyvinyl chloride and the toxicity of residual monomers. The use of these flexible bags, especially those made of non-rigid poly(vinyl chloride), however, involves possible problems caused by migration of plasticizers into the liquid contained in the bags and the toxicity of the vinyl chloride monomer contained in the poly(vinyl chloride).

A medical bag, wherein a polymer, such as an ethylene-vinyl acetate copolymer or an elastomer, was used as an intermediate layer, has been proposed as a medical bag having excellent flexibility, transparency and sanitariness (see Japanese Unexamined Patent Publication (Kokai) No. 58-165866). The heat resistance of the polymer used in the intermediate layer is so poor that wrinkles occur in the bag during thermal sterilization treatment, which deteriorates the appearance of the medical bag.

In view of the above, some of the present inventors have conducted various studies on a medical bag having excellent sanitariness, flexibility, transparency, heat resistance and suitable for use as a container for blood and medicinal liquids and, as a result, have found that the above-mentioned property requirements can be satisfied when the medical bag is composed of a sheet having a three-layer structure each comprising a polyethylene resin, and previously proposed (see Japanese Unexamined Patent Publication (Kokai) Nos. 62-44256 and 62-64363).

In the medical bag according to the invention described in the above-mentioned Japanese Unexamined Patent Publication (Kokai) No. 62-44256, the outer and inner surface layers each comprise a low-density polyethylene resin produced in the presence of a radical catalyst (the intermediate layer comprising a linear low-density polyethylene resin). Since, however, the outer surface layer of the proposed medical bag comprises a low-density polyethylene resin, the medical bag is not always satisfactory in heat resistance, so that the medical bag cannot be successfully subjected to a high-pressure steam treatment at a temperature of 120° C. For example, since the sealing strength is unsatisfactory, the medical bag cannot be successfully treated with a high-pressure steam sterilization treatment at a temperature of 120° C. for 20 minutes. The typical conditions of the high-pressure steam sterilization are, for example, 115° C.×30 minutes and 121° C.×20 minutes. Further, the medical bag is unsatisfactory also in the drop impact strength. Further, the flexibility and transparency lower, and some deformation occurs.

In order to solve these problems, some of the present inventors have proposed in Japanese Unexamined Patent Publication (Kokai) No. 4-266759 a method which enables the medical bag to withstand sterilization with a high-pressure steam at a high temperature of 121° C. through an improvement in the composition constituting the inner and outer layers. This method can surely provide a medical bag which gives rise to no significant deformation, is less subject to a lowering in the sealing strength and drop impact strength and can maintain the flexibility and transparency even when exposed to a high-pressure steam at a temperature of 121° C. in the sterilization, and enables molding to be stably conducted even in continuous production for a long period of time. Even the above-mentioned formulation caused a large amount of fine particles to sometimes elute into a liquid contained in the bag depending upon the type of contents after the sterilization with a high pressure steam at a temperature of 121° C. for 20 minutes, so that a sanitary problem may occur.

SUMMARY OF THE INVENTION

Accordingly, an object of the present invention is to provide a medical bag which gives rise to no significant deformation, can maintain the flexibility and transparency even when exposed to a high-pressure steam at 121° C. for 20 minutes in the sterilization, enables molding to be stably conducted even in continuous production for a long period of time, and is less liable to cause elution of a large amount of fine particles into the liquid contained in the bag.

Other objects and advantages of the present invention will be apparent from the following description.

In accordance with the present invention, there is provided a medical bag comprising a laminate film, sheet or tube composed of at least three layers comprising (i) an outer layer and an inner layer, at least said inner layer of the inner and outer layers in contact with a liquid contained in the bag comprises (a) a high-density polyethylene resin having a density of 0.945 g/cm$^3$ or more and an Mw/Mn value of 4.0 or less or (b) a composition comprising said high-density polyethylene resin and, added thereto, 60% by weight or less of a low-density polyethylene resin having a density of 0.930 g/cm$^3$ or less produced by a radical polymerization method; and (ii) an intermediate layer comprising a composition composed of a linear low-density polyethylene resin having a short-chain branching and a density of 0.920 g/cm$^3$ or less and, added thereto, 15% by weight or less of a high-density polyethylene resin having a density of 0.945 g/m$^3$ or more and an Mw/Mn value of 4.0 or less, said inner layer, intermediate layer and outer layer being in the following thickness relationship of a thickness ratio:

$$0.01 \leq (T_1+T_3)/(T_1+T_2+T_3) \leq 0.20$$

wherein $T_1$, $T_2$ and $T_3$ represent the thicknesses of the inner layer, intermediate layer and outer layer, respectively.

DESCRIPTION OF THE PREFERRED EMBODIMENT

The present inventors have conducted extensive and intensive studies with view to solving the above-described problems and, as a result, have found that an enhancement in the proportion of a high-density polyethylene having a density of 0.945 g/cm³ or more in at least a material constituting the inner layer is useful for preventing a large amount of fine particles from eluting into the liquid contained in the bag even when the bag is exposed to a high-pressure steam at a high temperature (121° C.).

As pointed out in Japanese Unexamined Patent Publication (Kokai) No. 4-266759, however, an increase in the high-density polyethylene content to 40% by weight or more gives rise to problems in respect of not only the molding stability in continuous production for a long period of time, but also a deterioration in the flexibility and transparency.

On Accordingly, the present inventors have found that, when the proportion of the thickness of the inner and outer layers, particularly the thickness of the inner layer, to the thickness of the intermediate layer is smaller than that in the conventional bag, even though the content of the high-density polyethylene resin in the inner layer is increased, the flexibility and transparency as the whole is not lost and a medical bag excellent in the molding stability in continuous production for a long period of time can be produced, which has led to the completion of the present invention.

The present invention will now be described in more detail.

The high-density polyethylene having a density of 0.945 g/cm³ or more and an Mw/Mn value of 4.0 or less, which is used in the present invention, is a polyethylene resin having a straight-chain structure and produced by homopolymerization of ethylene or copolymerization of ethylene with an α-olefin (e.g., propylene, butene-1, hexene-1, octene-1).

The density of the resin is 0.945 to 0.970 g/cm³, preferably 0.950 to 0.965 g/cm³, more preferably 0.952 to 0.960 g/cm³. The MFR of the resin is 0.1 to 20 g/10 min, preferably 0.2 to 10 g/10 min, more preferably 0.3 to 5.0 g/10 min. A great feature of this resin resides in a small molecular weight distribution, i.e., a small Mw/Mn value wherein Mw represents the weight-average molecular weight determined by GPC and Mn represents the number average molecular weight determined by GPC. That is, the molecular weight distribution should be narrow. When the Mw/Mn value exceeds 4, the transparency of the film, sheet, etc., remarkably deteriorates. The Mw/Mn value is in the range of from 4.0 to 2.2, preferably in the range of from 3.8 to 2.2, more preferably in the range of from 3.5 to 2.2.

Since the low-density polyethylene having a density of 0.930 g/cm³ or less and produced by a radical polymerization method is generally produced by polymerizing ethylene under a high pressure (usually 700 to 3000 kg/cm²), it is produced as a high-pressure polyethylene resin on a commercial scale.

The MFR value of the resin is 0.1 to 10 g/10 min, preferably 0.2 to 8.0 g/10 min, more preferably 0.3 to 5.0 g/10 min, determined by an ASTM method D1238, condition E. The density is 0.910 to 0.930 g/cm³, preferably 0.915 to 0.928 g/cm³, more preferably 0.918 to 0.927 g/cm³. When the density is less than 0.910 g/cm³, the resultant medical bag deforms during sterilization with high-pressure steam, so that wrinkles unfavorably occur.

The linear low-density polyethylene resins having a density of 0.920 g/cm³ or less, usable in the present invention, are those having a number of branching per 1000 carbon atoms in the main chain of 20 to 70, and the density thereof is 0.890 to 0.920 g/cm³. Further, the MFR value is 0.1 to 10 g/10 min. A peak of the melting point appears at 110° to 125° C. as determined by DSC.

The number of short-chain branching in the short chain per 1000 carbon atoms in the main chain is preferably 20 to 70, more preferably 30 to 70, particularly preferably 35 to 70. In the linear low-density polyethylene resin having the number of branching per 1000 carbon atoms in the main chain of less than 20, the flexibility becomes poor when it is molded into a film or a sheet, so that the use of the film or sheet as the medical bag of the present invention is unfavorable. On the other hand, a linear low-density polyethylene resin having a number of branching of more than 70 is not currently produced on a commercial scale.

The density of the linear low-density polyethylene resin in the present invention is 0.890 to 0.920 g/cm³, preferably 0.890 to 0.915 g/cm³, more preferably 0.890 to 0.910 g/cm³. A linear low-density polyethylene resin having a density of less than 0.890 g/cm³ is not currently produced on a commercial scale. On the other hand, when use is made of a linear low-density polyethylene resin having a density exceeding 0.920 g/cm³, the flexibility becomes poor when such a linear low-density polyethylene resin is molded into a film or sheet, so that the film or sheet is unfavorable as the medical bag according to the present invention. Further, the MFR value of the resin is preferably 0.1 to 10 g/10 min, more preferably 0.2 to 10 g/10 min, particularly preferably 0.3 to 5.0 g/10 min.

Sheet and its Production

In the production of the medical bag according to the present invention, a film or a sheet comprising the above-described layers is first prepared. The film or the sheet may be tubular.

In the sheet according to the present invention, the polyethylene resin used for constituting the individual layers should comprise the above-mentioned composition. The content of the high-density polyethylene resin having a density of 0.945 g/cm³ or more and an Mw/Mn value of 4.0 or less in the composition is 100 to 40% by weight, preferably 100 to 50% by weight, more preferably 100 to 70% by weight for the inner layer which comes into contact with the liquid contained in the bag. In the case of the inner layer, when the content of the high-density polyethylene is 40% by weight or less, a large amount of fine particles elute into the liquid contained in the bag.

On the other hand, in the case of the outer layer, although the content of the high-density polyethylene may be in the range of from 100 to 5% by weight, it is preferred that the content be relatively high when importance is placed on the heat resistance, while the content is relatively low when importance is placed on the flexibility, transparency and molding stability.

The proportion is preferably 15% by weight or less for the intermediate layer. In the case of the intermediate layer, when the proportion exceeds 15% by weight, although the heat resistance can be improved, the transparency and flexibility lower and further the molding stability becomes poor.

With respect to the thicknesses of individual layers constituting the film or sheet of the present invention, it is important that the thicknesses of the inner layer, intermediate layer and outer layer are in the following relationship of a thickness ratio:

$$0.01 \leq (T_1+T_3)/(T_1+T_2+T_3) \leq 0.20$$

wherein $T_1$, $T_2$ and $T_3$ respectively represent the thicknesses of the inner layer, intermediate layer and outer layer. When the ratio determined by the above formula, it is still preferably in the range of from 0.01 to 0.15, more preferably in the range of from 0.01 to 0.10. When the $(T_1+T_3)/(T_1+T_2+T_3)$ ratio is less than 0.01, since the thicknesses of the inner and outer layers are excessively thin, the heat resistance lowers, which causes fine particles to easily elute into the liquid contained in the bag. On the other hand, when the value is more than 0.20, although the heat resistance can be improved, the transparency and flexibility lower and further the molding stability in continuous production for a long period of time unfavorably deteriorates.

The thickness of the whole film or sheet is usually 0.10 to 0.80 mm, preferably 0.15 to 0.70 mm, more preferably 0.15 to 0.50 mm. When the thickness of the whole film or sheet is less than 0.10 mm, the impact strength is so low that there occurs a problem of practical use as a medical bag. On the other hand, when the thickness is more than 0.80 mm, the flexibility remarkably lowers, so that the practicability of the film or sheet as a medical bag is poor.

The film or sheet according to the present invention can be produced by blown-film co-extrusion (including a water-cooling system and an air-cooling system), T-die co-extrusion, dry lamination, extrusion lamination, and the like. From the economical standpoint, blown film co-extrusion and T-die co-extrusion are preferred.

Medical Bag and its Production

The medical bag of the present invention can be produced by forming a bag having predetermined shape and dimension through the application of a method used in the production of a general bag to the film or sheet thus obtained or a tubular material and mounting a port serving both as an outlet and an inlet (a connector plug).

EXAMPLES

The present invention will now be further illustrated by no means limited to, the following Examples.

In the Examples and Comparative Examples, the density was determined at a temperature of 23° C.±0.1° C. according to the JIS (Japanese Industrial Standard) K7112 method D.

The flexibility was determined in terms of Young's modulus according to ASTM D-882. The transparency was evaluated by filling the bag with a liquid, subjecting the bag to a sterilization treatment with a high-pressure steam at a temperate of 121° C. for 30 minutes, followed by measuring Haze according to the ASTM D-1003 method.

The visual appearance was evaluated according to the following four ranks.

⊙: Good

○: Fair

△: Slightly poor (Wrinkles and shrinkage occurred.)

X: Poor (Shrinkage occurred, and the deformation of the shape was observed.

The moldability was evaluated by conducting water-cooling co-extrusion inflation molding for forming a laminate comprising three different layers, and expressed in terms of the following three ranks.

○: Bubble was stable, and molding could be stably conducted with ease.

△: Bubble was unstable, and wrinkles were easily formed.

X: Bubble was so unstable that it was difficult to conduct continuous molding.

The number of fine particles was measured by preparing a testing solution according to Japanese Pharmacopoeia XII and subjecting the solution to measurement of the number of fine particles by means of an automatic particle counter manufactured by RION.

Examples 1 to 7 and Comparative Examples 1 to 6

Compositions in a pellet form were produced by selecting a plurality of combinations of two types of resins from a low-density polyethylene (abbreviated to "LDPE"), a high-density polyethylene (abbreviated to "HDPE") and a linear low-density polyethylene (abbreviated to "L-LDPE") respectively having densities specified in Table 1 so that the resultant compositions were different from each other in the content of components, mixing the components by means of a Henschel mixer for 5 minutes and kneading and extruding the resultant mixtures by means of three extruders having a diameter of 40 mm, 65 mm and 40 mm were used for inner, intermediate and outer layers, respectively, at a resin temperature of 180° C. into compositions in a pellet.

Medical bags having an internal volume of 500 ml were prepared from laminates formed by using the above-mentioned compositions, and evaluated by the above-mentioned methods. The results are given in Table 2.

TABLE 1

| | | | Composition of Film | | | | | | | |
|---|---|---|---|---|---|---|---|---|---|---|
| | | | Inner layer | | | | | Intermediate layer | | |
| Ex. and Comp. Ex. | Total thickness (μm) | Thickness $T_1$ (μm) | LDPE | | HDPE | | | Thickness $T_2$ (μm) | L-LDPE | |
| | | | Density | Proportion (%) | Density | Proportion (%) | Mw/Mn | | Density | Proportion (%) |
| Ex. 1 | 250 | 5 | — | 0 | 0.949 | 100 | 3.5 | 240 | 0.900 | 95 |
| Ex. 2 | 250 | 10 | — | 0 | 0.953 | 100 | 3.2 | 225 | 0.900 | 100 |
| Ex. 3 | 250 | 10 | — | 0 | 0.953 | 100 | 3.2 | 225 | 0.900 | 95 |
| Ex. 4 | 300 | 15 | 0.920 | 50 | 0.953 | 50 | 3.2 | 270 | 0.900 | 90 |
| Ex. 5 | 350 | 10 | 0.920 | 50 | 0.953 | 50 | 3.2 | 330 | 0.910 | 95 |

TABLE 1-continued

Composition of Film

|  |  |  |  |  |  |  |  |  |  |  |
|---|---|---|---|---|---|---|---|---|---|---|
| Ex. 6 | 400 | 10 | 0.926 | 30 | 0.949 | 70 | 3.5 | 370 | 0.910 | 95 |
| Ex. 7 | 450 | 40 | 0.920 | 50 | 0.953 | 50 | 3.2 | 370 | 0.895 | 90 |
| Comp. Ex. 1 | 250 | 10 | 0.920 | 90 | 0.953 | 10 | 3.2 | 230 | 0.900 | 95 |
| Comp. Ex. 2 | 250 | 15 | 0.920 | 95 | 0.953 | 5 | 3.2 | 225 | 0.900 | 100 |
| Comp. Ex. 3 | 250 | 15 | 0.920 | 80 | 0.953 | 20 | 3.2 | 220 | 0.910 | 80 |
| Comp. Ex. 4 | 500 | 2 | 0.920 | 50 | 0.949 | 50 | 3.5 | 496 | 0.910 | 90 |
| Comp. Ex. 5 | 400 | 50 | — | 0 | 0.949 | 100 | 3.5 | 300 | 0.895 | 95 |
| Comp. Ex. 6 | 300 | 30 | 0.926 | 70 | 0.960 | 30 | 5.5 | 270 | 0.910 | 95 |

| | Intermediate layer | | | | Outer layer | | | | | |
|---|---|---|---|---|---|---|---|---|---|---|
| | HDPE | | | Thick | LPDE | | HPDE | | | |
| Ex. and Comp. Ex. | Density | Proportion (%) | Mw/Mn | ness $T_3$ (μm) | Density | Proportion (%) | Density | Proportion (%) | Mw/Mn | Thickness ratio |
| Ex. 1 | 0.949 | 5 | 3.5 | 5 | — | 0 | 0.949 | 100 | 3.5 | 0.04 |
| Ex. 2 | — | 0 | 3.2 | 15 | 0.920 | 70 | 0.953 | 30 | 3.2 | 0.10 |
| Ex. 3 | 0.953 | 5 | 3.2 | 15 | 0.920 | 70 | 0.953 | 30 | 3.2 | 0.10 |
| Ex. 4 | 0.953 | 10 | 3.2 | 15 | 0.920 | 70 | 0.953 | 30 | 3.2 | 0.10 |
| Ex. 5 | 0.953 | 5 | 3.2 | 10 | 0.920 | 50 | 0.953 | 50 | 3.2 | 0.06 |
| Ex. 6 | — | 5 | 3.5 | 20 | 0.926 | 90 | 0.949 | 10 | 3.5 | 0.08 |
| Ex. 7 | 0.953 | 10 | 3.2 | 40 | 0.920 | 70 | 0.953 | 30 | 3.2 | 0.18 |
| Comp. Ex. 1 | 0.953 | 5 | 3.2 | 10 | 0.920 | 90 | 0.953 | 10 | 3.2 | 0.08 |
| Comp. Ex. 2 | — | 0 | 3.2 | 10 | — | 0 | 0.953 | 100 | 3.2 | 0.10 |
| Comp. Ex. 3 | 0.953 | 20 | 3.2 | 15 | 0.920 | 15 | 0.953 | 85 | 3.2 | 0.12 |
| Comp. Ex. 4 | 0.949 | 10 | 3.5 | 2 | 0.920 | 70 | 0.949 | 30 | 3.5 | 0.008 |
| Comp. Ex. 5 | 0.949 | 5 | 3.5 | 50 | 0.926 | 70 | 0.949 | 30 | 3.5 | 0.25 |
| Comp. Ex. 6 | 0.960 | 5 | 5.5 | 15 | 0.926 | 70 | 0.960 | 30 | 3.5 | 0.10 |

TABLE 2

Product Property and Fabrication Property of Film

| | Product Property (after retort treatment at 121° C. for 30 min) | | | | |
|---|---|---|---|---|---|
| Ex. and Comp. Ex. | Transparency Haze (%) | Flexibility (Young's modulus) (kg/cm$^2$) | Appearance (deformation) | Number of fine particles[1] particles/10 ml | Moldability |
| Ex. 1 | 15 | 1500 | ⊙ | 50 | ○ |
| Ex. 2 | 18 | 1400 | ○ | 63 | ○ |
| Ex. 3 | 11 | 1900 | ⊙ | 45 | ○ |
| Ex. 4 | 19 | 2100 | ⊙ | 97 | ○ |
| Ex. 5 | 14 | 1500 | ⊙ | 88 | ○ |
| Ex. 6 | 21 | 1300 | ⊙ | 73 | ○ |
| Ex. 7 | 27 | 2000 | ⊙ | 90 | ○ |
| Comp. Ex. 1 | 23 | 2200 | X | 495 | ○ |
| Comp. Ex. 2 | 38 | 1900 | Δ | 560 | ○ |
| Comp. Ex. 3 | 29 | 3900 | ○ | 380 | Δ |
| Comp. Ex. 4 | 28 | 1700 | X | 320 | ○ |
| Comp. Ex. 5 | 67 | 3400 | ⊙ | 49 | X |
| Comp. Ex. 6 | 65 | 2600 | ○ | 290 | ○ |

Note)
[1] Fine particle: number of fine particles having a size of 2 μm or more per 10 ml.

As is apparent from the above-described Examples and Comparative Examples, only medical bags produced by using a laminate comprising a composition falling within a particular composition range are excellent in the transparency, flexibility, visual appearance after a retort treatment at 121° C. and prevention of elution of fine particles, and exhibit good results in continuous molding.

The medical bag of the present invention is not only excellent in the sanitariness, transparency and flexibility but also can be continuously molded and exhibits a satisfactory heat resistance even in a retort treatment at 121° C. for 30 minutes, which renders the medical bag of the present invention useful as a medical bag for a high temperature sterilization.

We claim:

1. A sterilizable medical bag comprising a laminate film, sheet or tube having at least the following three layers:

(i) an outer layer;

(ii) an inner layer, wherein said inner layer contacts the contents of said medical bag, and wherein said inner layer comprises:

(a) a high-density polyethylene resin having a density of not less than 0.945 g/cm$^3$ and an Mw/Mn ratio of 2.2 to 3.5; or (b) a composition comprising an admixture of said high-density polyethylene resin, and not more than 60% by weight of a low-density polyethylene resin having a density of not more than 0.930 g/cm$^3$ obtainable by radical polymerization; and (iii) an intermediate layer between said inner layer and said outer layer, and comprising a composition comprising an admixture of a linear low-density polyethylene resin having short-chain branching and a density of not more than 0.920 g/cm$^3$, and not more than 15% by weight of a high-density polyethylene resin having a density of not less than 0.945 g/cm$^3$ and an Mw/Mn value of not more than 4.0;

and wherein said inner layer, intermediate layer and outer layer have the following thickness ratio relationship:

$$0.01 \leq (T_1+T_3)/(T_1+T_2+T_3) \leq 0.10$$

wherein $T_1$, $T_2$ and $T_3$ represent the thickness of said inner layer, intermediate layer and outer layer, respectively.

2. A medical bag as claimed in claim 1, wherein the density of the high-density polyethylene is 0.945 to 0.970 g/cm$^3$.

3. A medical bag as claimed in claim 1, wherein an MFR of the high-density polyethylene resin is 0.1 to 20 g/10 min.

4. A medical bag as claimed in claim 1, wherein the density of the low-density polyethylene resin of the inner layer is 0.910 to 0.930 g/cm$^3$.

5. A medical bag as claimed in claim 1, wherein an MFR of the low-density polyethylene resin of the inner layer is 0.1 to 10 g/10 min.

6. A medical bag as claimed in claim 1, wherein the composition for the inner layer comprises 100 to 40% by weight of the high-density polyethylene resin and 60% by weight or less of the low-density polyethylene resin.

7. A medical bag as claimed in claim 1, wherein the number of the short-chain branching in the short branching is 20 to 70 per 1000 carbon atoms.

8. The medical bag recited in claim 1, wherein said outer layer comprises:

(i) a high-density polyethylene resin having a density of not less than 0.945 g/cm$^3$, and an Mw/Mn ratio of 2.2 to 3.5; or (ii) a composition comprising an admixture of said high-density polyethylene resin, and not more than 60% by weight of a low-density polyethylene resin having a density of not more than 0.930 g/cm$^3$ obtainable by radical polymerization.

9. A medical bag as claimed in claims 1, wherein the total thickness of the at least three layers is 0.1–0.8 mm.

* * * * *